United States Patent [19]

Sonnabend

[11] 4,384,096
[45] May 17, 1983

[54] LIQUID EMULSION POLYMERS USEFUL AS PH RESPONSIVE THICKENERS FOR AQUEOUS SYSTEMS

[75] Inventor: Lawrence F. Sonnabend, Midland, Mich.

[73] Assignee: The Dow Chemical Company, Midland, Mich.

[21] Appl. No.: 219,480

[22] Filed: Dec. 23, 1980

Related U.S. Application Data

[63] Continuation of Ser. No. 70,061, Aug. 27, 1979, abandoned, which is a continuation-in-part of Ser. No. 964,113, Nov. 27, 1978, abandoned.

[51] Int. Cl.³ .................. C08F 20/30; C08F 20/28; C08F 20/06
[52] U.S. Cl. .................. 526/313; 524/522; 524/558; 526/317; 526/318
[58] Field of Search .................. 260/29.6 H, 29.6 TA, 260/29.6 RW; 526/313, 317, 318, 320

[56] References Cited

U.S. PATENT DOCUMENTS

| | | | |
|---|---|---|---|
| 3,657,175 | 4/1972 | Zimmerman | 260/29.6 T |
| 3,891,591 | 6/1975 | Chang | 260/29.6 WB |
| 3,894,980 | 7/1975 | De Tommaso | 260/29.6 RW |
| 4,077,926 | 3/1978 | Sanderson | 260/29.6 TA |
| 4,138,381 | 2/1979 | Chang | 260/29.6 TA |

*Primary Examiner*—Paul R. Michl

[57] ABSTRACT

Novel aqueous liquid emulsion polymers are prepared by the copolymerization of (A) about 15–60 weight percent of a $C_3$–$C_8$ $\alpha,\beta$-ethylenically unsaturated carboxylic acid monomer, preferably acrylic or methacrylic acid or a mixture thereof with itaconic or fumaric acid, (B) about 15–80 weight percent of a nonionic copolymerizable $C_2$–$C_{12}$ $\alpha,\beta$-ethylenically unsaturated monomer, preferably a monovinyl ester such as ethyl acrylate or a mixture thereof with styrene, acrylonitrile, vinyl chloride or vinyl acetate, and (C) about 1–30 weight percent of certain nonionic vinyl surfactant esters, such as nonylphenoxypoly(ethyleneoxy)$_9$ ethyl acrylate, to give an emulsion copolymer stable as an aqueous colloidal dispersion at an acid pH lower than about 5.0 but responsive to pH adjustment with base. These emulsion polymers adjusted to a pH of about 5.5 or higher are effective thickeners for a wide variety of aqueous systems including cosmetic products, drilling muds, and particularly aqueous coating compositions such as latex paint.

30 Claims, 1 Drawing Figure

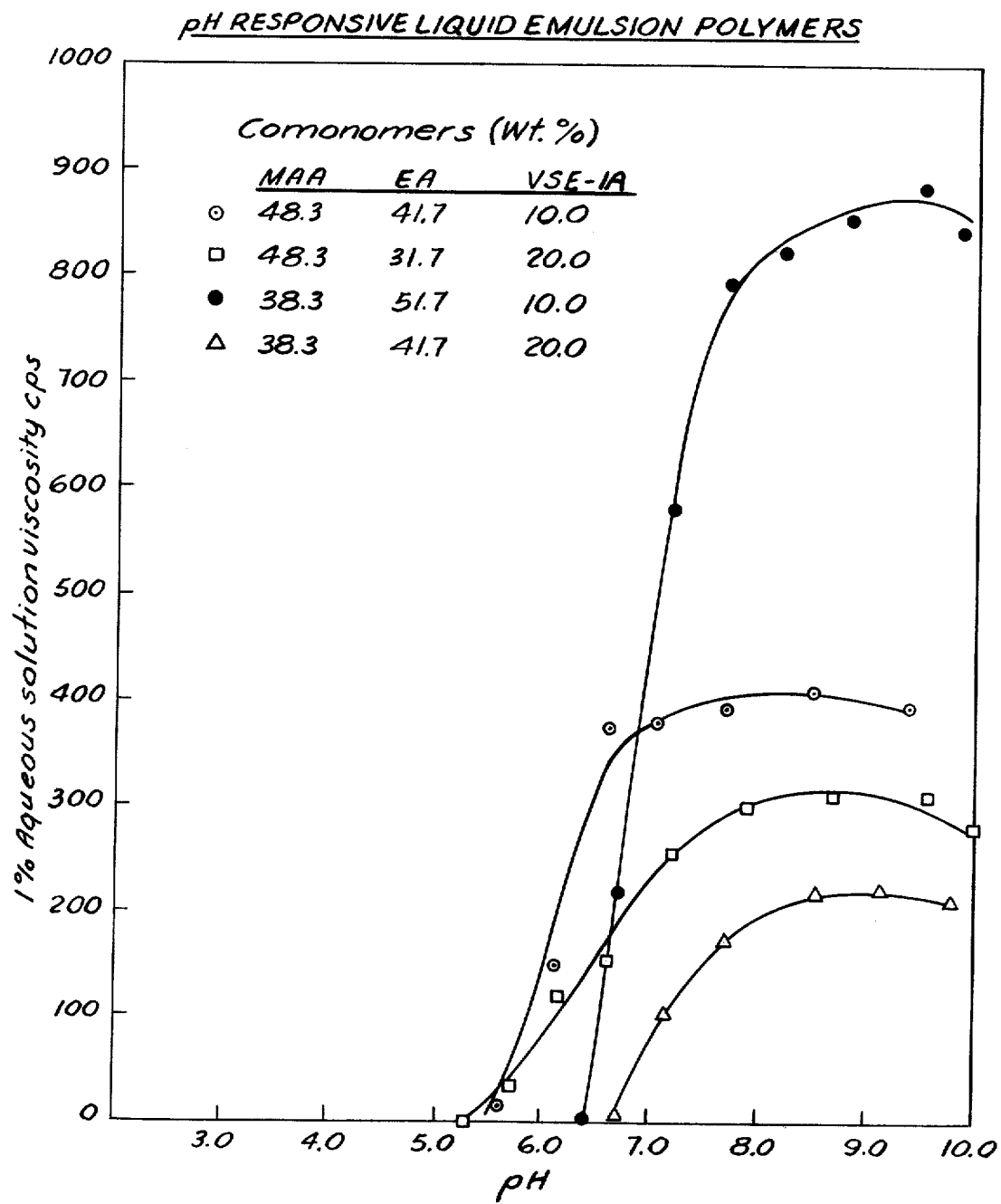

LIQUID EMULSION POLYMERS USEFUL AS pH RESPONSIVE THICKENERS FOR AQUEOUS SYSTEMS

CROSS-REFERENCE TO RELATED APPLICATIONS

This application is a continuation of application Ser. No. 070,061, filed Aug. 27, 1979 now abandoned which in turn is a continuation-in-part of application Ser. No. 964,113, filed Nov. 27, 1978, now abandoned.

BACKGROUND OF THE INVENTION

Polymeric water-soluble thickening agents are widely known and used in many aqueous systems including latex paints and other aqueous coating compositions.

The widespread use of latex paints, i.e., paints based on aqueous dispersions of synthetic organic polymers, has prompted continued research on product and process improvements. One particularly important concern is controlling the paint rheology to obtain proper flow and leveling with a minimum of dripping and spattering. Cellulose ethers, such as described in Glomski et al. U.S. Pat. No. 3,769,247, are often effectively used as thickeners for latex paints. However solid, water-soluble polymers derived from cellulose and other natural products are becoming increasingly expensive to produce because of high capital, energy, and waste control costs.

Alkali soluble latex copolymers have been known for some time. Thus, Hager and Martin U.S. Pat. Nos. 3,003,987 and 3,070,561 and Miller U.S. Pat. No. 3,081,198 describe copolymers of acrylic and methacrylic acids and esters which may be thickened by replacing a portion of the hydrogen ions of the copolymer carboxyl groups with ammonium or alkali metal ions. Other types of polymeric thickeners are disclosed by Junas and LaTorre U.S. Pat. Nos. 3,652,497 and 3,708,445, Zimmerman U.S. Pat. No. 3,657,175, Chang and McDowell U.S. Pat. No. 3,891,591, and Gibson U.S. Pat. No. 4,003,870. All contain various carboxylic acid groups which can be solubilized in water by neutralization with a water-soluble base. However, to date this technology has had limited impact on major markets for water-soluble polymeric thickeners.

More recently, Evani and Corson developed, as described in U.S. Pat. No. 4,008,202 and related patents, a solid styrene-maleic anhydride-vinylbenzyl ether terpolymer soluble at high pH and useful as a thickener for aqueous solutions. In spite of excellent rheology, stability problems and cost have limited its use as a paint thickener. Further improvements in this technology are clearly desirable.

SUMMARY OF THE INVENTION

New aqueous emulsion polymers have been discovered which provide stable liquid emulsions having low viscosity and relatively high solids content under acidic conditions, but which become very efficient polymeric thickeners for many aqueous systems when treated with base. These new products are preferably prepared in the form of an aqueous colloidal dispersion of water-insoluble polymer by emulsion polymerization at a pH of about 2.5 to 5.0 of three essential ethylenically unsaturated monomeric components: (A) a carboxylic acid monomer, (B) a nonionic vinyl monomer and (C) a nonionic vinyl surfactant ester.

More specifically, a polymer useful as a pH responsive thickener for aqueous systems has been developed comprising an aqueous emulsion copolymer of:

A. about 15–60 weight percent based on total monomers of at least one $C_3$–$C_8$ $\alpha,\beta$-ethylenically unsaturated carboxylic acid monomer of the formula:

$$RCH=\underset{\underset{R'}{|}}{C}-COOH \qquad (I)$$

where
R is H and R' is H, $C_1$–$C_4$ alkyl, or —$CH_2COOX$;
R is —COOX and R' is H or —$CH_2COOX$; or
R is $CH_3$ and R' is H; and
X is H or $C_1$–$C_4$ alkyl;

B. about 15–80 weight percent of at least one nonionic, copolymerizable $C_2$–$C_{12}$ $\alpha,\beta$-ethylenically unsaturated monomer of the formula:

$$CH_2=CYZ \qquad (II)$$

where
Y is H and Z is —COOR, —$C_6H_4R'$, CN, Cl,

$$-O\overset{O}{\underset{\|}{C}}R''$$

or —$CH=CH_2$;
Y is $CH_3$ and Z is —COOR, —$C_6H_4R'$, CN or —$CH=CH_2$; or
Y and Z are Cl; and
R is $C_1$–$C_8$ alkyl or $C_2$–$C_8$ hydroxyalkyl;
R' is H, Cl, Br, or $C_1$–$C_4$ alkyl; and
R'' is $C_1$–$C_8$ alkyl; and C. about 1–30 weight percent based on total monomers of at least one nonionic vinyl surfactant ester of the formula:

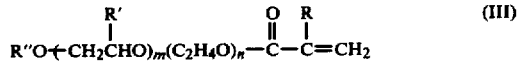

$$R''O\text{-}(CH_2CHO)_m(C_2H_4O)_n\text{-}\underset{\underset{R'}{|}}{\overset{\overset{O}{\|}}{C}}-\underset{\underset{}{|}}{\overset{\overset{R}{|}}{C}}=CH_2 \qquad (III)$$

where
R is H or $CH_3$, each R' is $C_1$–$C_2$ alkyl,
R'' is $C_8$–$C_{20}$ alkyl or $C_8$–$C_{16}$ alkylphenyl,
n is an average number from about 6–100 and m is an average number from about 0–50 provided that $n \geq m$ and $\Sigma(n+m)$ is about 6–100; said polymer being stable as an aqueous colloidal dispersion at a pH lower than about 5.0 but becoming an effective thickener for aqueous systems upon adjustment to a pH of about 5.5–10.5 or higher.

The emulsion polymerization is normally carried out under acidic conditions in which the carboxylic acid groups are in protonated form to insolubilize the polymer and give a liquid emulsion. When the polymeric thickener is added as such a liquid colloidal dispersion, the finely divided polymer particles dissolve almost instantly upon pH adjustment. The ease of handling, metering, and dispersing the liquid emulsion polymer, the rapid solubilization by controlled pH adjustment, and the highly desirable rheological properties make this liquid emulsion polymer a most effective and efficient thickening agent for a wide variety of applications including latex paints and other aqueous coating compositions.

DETAILED DESCRIPTION OF THE INVENTION

1. Essential Monomeric Components

The novel liquid emulsion polymers of this invention require three essential components: (A) about 15–60 weight percent of a $C_3$–$C_8$ $\alpha,\beta$-ethylenically unsaturated carboxylic acid monomer, (B) about 15–80 weight percent of a copolymerizable nonionic vinyl monomer, and (C) about 1–30 weight percent of certain nonionic vinyl surfactant esters. It has been discovered that the effectiveness of these liquid emulsion polymers as a pH responsive thickener for many aqueous products is critically dependent on these components. The acid component A provides the requisite pH responsiveness; the nonionic vinyl comonomer B provides an extended polymer backbone and added hydrophiliclipophilic balance; and the nonionic vinyl surfactant ester C provides an in situ, bound surfactant to control the rheology of the aqueous system containing the solubilized polymeric thickener. Within the stated limits, the proportions of the individual monomers can be varied to achieve optimum properties for specific applications.

A. Carboxylic Acid Monomer

The liquid emulsion polymer requires about 15–60 weight percent based on total monomers of a $C_3$–$C_8$ $\alpha,\beta$-ethylenically unsaturated carboxylic acid monomer of the formula:

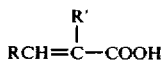  (I)

where
R is H and R' is H, $C_1$–$C_4$ alkyl, or —$CH_2COOX$; R is —COOX and R' is H or —$CH_2COOX$; or R is $CH_3$ and R' is H; and X is H or $C_1$–$C_4$ alkyl.

Acrylic or methacrylic acid or a mixture thereof with itaconic or fumaric acid are preferred, but crotonic and aconitic acid and half esters of these and other polycarboxylic acids such as maleic acid with $C_1$–$C_4$ alkanols are also suitable, particularly if used in minor amount in combination with acrylic or methacrylic acid. For most purposes, it is preferable to have at least about 25 weight percent and most preferably from about 35–55 weight percent of the carboxylic acid monomer. However, polycarboxylic acid monomers and half esters can be substituted for a portion of the acrylic or methacrylic acid, e.g., about 1–15 weight percent based on total monomers.

B. Nonionic Vinyl Monomer

To provide the extended polymer backbone and body needed for effective thickening requires about 15–80 weight percent of at least one copolymerizable nonionic $C_2$–$C_{12}$ $\alpha,\beta$-ethylenically unsaturated monomer selected from the group consisting of the formula:

$$CH_2=CYZ \quad (II)$$

where
Y is H and Z is —COOR, —$C_6H_4R'$, CN, Cl,

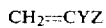

or —$CH=CH_2$;
Y is $CH_3$ and Z is —COOR, —$C_6H_4R'$, CN or —$CH=CH_2$; or
Y and Z are Cl; and
R is $C_1$–$C_8$ alkyl or $C_2$–$C_8$ hydroxyalkyl;
R' is H, Cl, Br, or $C_1$–$C_4$ alkyl;
R" is $C_1$–$C_8$ alkyl.

Typical of such monomers are the $C_1$–$C_8$ alkyl and $C_2$–$C_8$ hydroxyalkyl esters of acrylic and methacrylic acid including ethyl acrylate, ethyl methacrylate, methyl methacrylate, 2-ethylhexyl acrylate, butyl acrylate, butyl methacrylate, 2-hydroxyethyl acrylate, 2-hydroxybutyl methacrylate; styrene, vinyltoluene, t-butylstyrene, isopropylstyrene, and p-chlorostyrene; vinyl acetate, vinyl butyrate, vinyl caprolate; acrylonitrile, methacrylonitrile, butadiene, isoprene, vinyl chloride, vinylidene chloride, and the like. In practice, a monovinyl ester such as ethyl acrylate or a mixture thereof with styrene, hydroxyethyl acrylate, acrylonitrile, vinyl chloride or vinyl acetate is preferred.

These monomers, of course, must be copolymerizable with the carboxylic acid and vinyl surfactant ester comonomers. Normally about 15–80 weight percent, and preferably about 20–60 weight percent of nonionic vinyl monomer, based on total weight of monomers, is used in preparing the liquid emulsion polymer.

C. Nonionic Vinyl Surfactant Ester

The third required monomer component is about 1–30 weight percent based on total monomers of a nonionic vinyl surfactant ester of the formula:

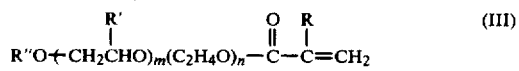  (III)

where
R is H or $CH_3$; each R' is $C_1$–$C_2$ alkyl; R" is $C_8$–$C_{20}$ alkyl or $C_8$–$C_{16}$ alkylphenyl; n is an average number from about 6–100 and m is an average number from about 0–50 provided that $n \geq m$ and $\Sigma(n+m)$ is about 6–100.

Preferred are the acrylate and methacrylate surfactant esters selected from the group consisting of:

(1) alkylphenoxypoly(ethyleneoxy)ethyl acrylates of the formula:

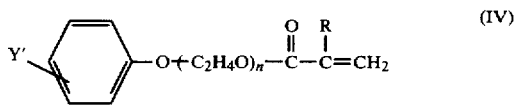  (IV)

where
R is H or $CH_3$; Y' is $C_8$–$C_{16}$ alkyl, and n is about 6–100;

(2) alkoxypoly(ethyleneoxy)ethyl acrylates of the formula:

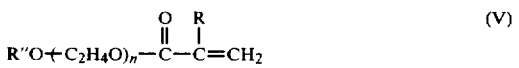  (V)

where
R is H or $CH_3$, R" is $C_8$–$C_{20}$ alkyl, and n is about 6–50; and (3) alkoxypoly(alkyleneoxy)ethyl acrylates of the formula:

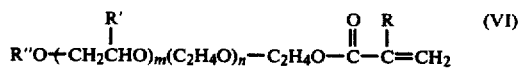

where

R is H or CH$_3$, each R' is C$_1$–C$_2$ alkyl, R" is C$_8$–C$_{20}$ alkyl, and n is about 6–50 and m is about 1–40.

These essential vinyl surfactant esters are the acrylic or methacrylic acid esters of certain nonionic surfactant alcohols. Such surfactant esters are known in the art. For example, Junas et al. U.S. Pat. No. 3,652,497 describe the use of alkylphenoxyethyleneoxyethyl acrylates in preparing several other polymeric surfactant thickeners. Dickstein U.S. Pat. No. 4,075,411 describes several processes for preparing such vinyl surfactant esters including the acid catalyzed condensation of commercially available nonionic polyoxyalkylene surfactant alcohols such as alkylphenoxypoly(ethyleneoxy)ethyl alcohol and block-polymeric glycols with acrylic, methacrylic, crotonic, maleic, fumaric, itaconic or aconitic acid. Alternate esterification methods including alcoholysis and transesterification are also described. Other suitable vinyl surfactant esters can be prepared from monoethers of mixed or heteric ethyleneoxypropyleneoxy-butyleneoxy polyglycols such as described in Patton U.S. Pat. No. 2,786,080. Additional surfactant alcohols which can be esterified for use herein are given in "McCutcheon's Detergents and Emulsifiers" 1973, North American Edition, Allured Publishing Corp., Ridgewood, N.J. 07450.

Certain of these vinyl surfactant esters, i.e., those defined by Formula III and particularly the alkylphenoxy and alkoxyethyl esters of Formulas IV–VI, are useful in preparing the novel emulsion polymers described herein. It is essential that the surfactant be incorporated in the liquid emulsion product by copolymerization. Advantageously the requisite surfactant esters are prepared by the direct acid catalyzed esterification of the appropriate surfactant alcohol with an excess of the carboxylic acid monomer used as Component A. The resulting mixture with excess acid can be used directly in the copolymerization provided that at least 30 percent, and preferably 50–70 percent or more, of the surfactant alcohol in the mixture is esterified. The vinyl surfactant ester can also be recovered, purified by conventional means using an appropriate inhibitor such as hydroquinone or p-tert-butylcatechol to prevent undesired homopolymerization, and then used to prepare the liquid emulsion polymers.

It has been found that the hydrophilic-lipophilic balance (HLB) of the vinyl surfactant ester is an important factor in the performance of the resulting emulsion polymer. Thus for a given polyethyleneoxy content, increasing the chain length of the terminal hydrophobic alkoxy or alkylphenoxy group will increase the efficiency of the resulting polymer as a thickener. Also for a given lipophilic group decreasing the number of polyethyleneoxy groups increases thickener efficiency. For many surfactant esters usable herein an average of about 10–40 ethyleneoxy groups (e.g., Formula III, n = 10–40) is preferred.

Also it has been found that the hydrophilic balance of the copolymer product can be adjusted to a degree by the judicious selection of the nonionic vinyl monomer B; e.g., a soft, (lower alkyl)poly(ethyleneoxy)ethyl ester of Formula VI can be used in a system with mixture of ethyl acrylate and a hard comonomer such as styrene.

However, it is critical to the performance of these products that they contain an effective amount of an in situ, bound surfactant to control the rheology of the aqueous system thickened with the solubilized emulsion polymer.

2. Copolymerization

A. The novel liquid emulsion copolymers are conveniently prepared from the above-described monomers by conventional emulsion polymerization at an acid pH lower than about 5.0 using free-radical producing initiators, usually in an amount from 0.01 percent to 3 percent based on the weight of the monomers. The free-radical producing initiators conveniently are peroxygen compounds especially inorganic persulfate compounds such as ammonium persulfate, potassium persulfate, sodium persulfate; peroxides such as hydrogen peroxide; organic hydroperoxides, for example, cumene hydroperoxide, t-butyl hydroperoxide; organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite); as well as other free-radical producing materials such as 2,2'-azobisisobutyronitrile.

Optionally, a chain transfer agent and an additional emulsifier can be used. Representative chain transfer agents are carbon tetrachloride, bromoform, bromotrichloromethane, long chain alkyl mercaptans and thioesters such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate. The chain transfer agents are used in amounts up to about 10 parts per 100 parts of polymerizable monomers.

Often at least one anionic emulsifier is included in the polymerization charge and one or more of the known nonionic emulsifiers may also be present. Examples of anionic emulsifiers are the alkali metal alkyl aryl sulfonates, the alkali metal alkyl sulfates and the sulfonated alkyl esters. Specific examples of these well-known emulsifiers are sodium dodecylbenzenesulfonate, sodium disecondary-butylnaphthalene sulfonate, sodium lauryl sulfate, disodium dodecyldiphenyl ether disulfonate, disodium n-octadecylsulfosuccinamate and sodium dioctylsulfosuccinate.

Optionally, other ingredients well known in the emulsion polymerization art may be included such as chelating agents, buffering agents, inorganic salts and pH adjusting agents.

Polymerization at an acid pH lower than about 5.0 permits direct preparation of an aqueous colloidal dispersion with relatively high solids content without problems of undue viscosity.

Usually the copolymerization is carried out at a temperature between about 60° C. and 90° C. but higher or lower temperatures may be used. The polymerization is carried out batchwise, stepwise or continuously with batch and/or continuous addition of the monomers in a conventional manner.

B. The essential monomers can be copolymerized in such proportions, and the resulting emulsion polymers can be physically blended, to give products with the desired balance of properties for specific applications. For example, if a more viscous product is desired, the acid and surfactant monomer content can be increased. Greater flexibility and coalescence can be obtained with higher amounts of ethyl acrylate. Addition of styrene as a second nonionic vinyl monomer will increase to a higher pH the adjustment required to dissolve the emulsion in an aqueous coating composition. Minor quantities of a polyfunctional monomer, such as itaconic or fumaric acid or isoprene to introduce a higher carboxylic acid content or limited crosslinking, provides further control on the solubility of the emulsion polymer after pH adjustment. Thus, by varying the monomers and their proportions, emulsion polymers having optimum properties for particular applications can be designed.

In practice it is normally desirable to copolymerize about 15–60 weight percent based on total monomers (more desirably from about 25–60 weight percent, preferably about 35–55 percent, and most preferably about 40–50 percent) of the carboxylic acid monomer A, about 15–80 weight percent (preferably about 20–60 percent, and most preferably about 35–50 percent), of the nonionic vinyl monomer B and about 1–30 weight percent (preferably about 2–20 percent, and most preferably about 2–12 percent) of the nonionic vinyl surfactant ester C. Particularly effective liquid emulsion polymer thickeners are obtained by copolymerization of about 40–50 weight percent of methacrylic acid, about 35–50 weight percent of ethyl acrylate, and about 2–12 weight percent of the methacrylic ester of a $C_9$-alkylphenoxy(ethyleneoxy)$_9$ ethyl alcohol.

3. Copolymer Properties

The copolymer products prepared by emulsion polymerization at an acid pH are in the form of stable aqueous colloidal dispersions usually with a typical milky latex appearance. Such a liquid emulsion contains the copolymer dispersed as discrete particles having average particle diameters of about 500–3000 Å, preferably about 1000–1750 Å, as measured by light refraction. Dispersions containing polymer particles smaller than about 500 Å are difficult to stabilize while particles larger than about 3000 Å reduce the ease of dispersion in the aqueous products to be thickened.

These emulsion copolymers will normally have number average molecular weights of at least about 30,000 as determined by gel permeation chromatography. To provide most effective thickening with copolymers which are water-soluble when neutralized, molecular weights within the range of about 200,000 to 5,000,000 are preferred. In terms of a standard Brookfield viscosity measured as a 1 percent aqueous solution in ammonium salt form at pH 9 and 25° C., a copolymer with a viscosity of about 50–50,000 cps, and preferably about 100–30,000 cps, is particularly desirable for many applications.

In the form of a stable, aqueous colloidal dispersion at an acid pH of about 2.5–5.0 the copolymer is particularly useful. Such aqueous dispersion may contain about 10–50 weight percent of polymer solids yet be of relatively low viscosity. Thus it is readily metered and blended with aqueous product systems. However, the dispersion is pH responsive. When the pH of the polymer dispersion is adjusted by addition of a base such as ammonia, an amine or a non-volatile inorganic base such as sodium hydroxide, potassium carbonate or the like, the aqueous mixture becomes translucent or transparent as the polymer dissolves at least partially in the aqueous phase with a concurrent increase in viscosity. This neutralization can occur in situ when the liquid emulsion polymer is blended with an aqueous solution containing a suitable base. Or if desired for a given application, pH adjustment by partial or complete neutralization can be carried out before or after blending the liquid emulsion polymer with an aqueous product.

The term "liquid emulsion polymer" as applied to the new thickener of this specification means that the thickener is an emulsion polymer because the polymer was prepared by emulsion polymerization even though the polymer per se may be (and generally is) a solid at room temperature but is a "liquid" emulsion polymer because it is in the form of a liquid solution or dispersion.

The pH viscosity response curves for several typical liquid emulsion polymers prepared by copolymerizing methacrylic acid (MAA), ethyl acrylate (EA), and nonylphenoxypoly(ethyleneoxy)$_9$ethyl methacrylate (VSE-1A) are shown in the FIGURE as determined in aqueous media at a concentration of 1 percent by weight and at room temperature. Note that the pH range of initial viscosity build can be controlled by variation in the composition of the emulsion copolymer.

These emulsion polymers are useful as water-soluble thickeners for a wide variety of applications ranging from cosmetics to drilling muds, but particularly for aqueous coating compositions.

4. Use as A Thickener

The liquid emulsion polymers described herein are particularly useful as thickeners for a wide variety of water-based compositions including aqueous brine and polymer solutions as well as aqueous slurries and colloidal dispersions of water-insoluble inorganic and organic material including compositions such as natural rubber, synthetic or artificial latexes and aqueous products containing such materials.

Synthetic latexes which may be thickened with the liquid emulsion polymers are aqueous colloidal dispersions of water-insoluble polymers prepared by emulsion polymerization of one or more ethylenically unsaturated monomers. Typical of such synthetic latexes are emulsion copolymers of monoethylenically unsaturated compounds such as styrene, methyl methacrylate, acrylonitrile with a conjugated diolefin such as butadiene or isoprene; copolymers of styrene, acrylic and methacrylic esters, copolymers of vinyl halide, vinylidene halide, vinyl acetate and the like. Many other ethylenically unsaturated monomers or mixtures thereof can be emulsion polymerized to form synthetic latexes. Representative monomers are vinyl aromatic monomers such as styrene, α-methylstyrene, t-butylstyrene, chlorostyrene, vinyltoluene; conjugated dienes such as butadiene, isoprene, and 2-chloro-1,3-butadiene; vinyl chloride, vinylidene chloride, acrylonitrile, and methacrylonitrile; acrylic and β-hydroxyalkyl acrylic esters; vinyl acetate, vinyl propionate, ethylene and methyl isopropenyl ketone. Also limited amounts of unsaturated carboxylic acid monomers such as defined by Formula I are frequently used in preparing the base polymer for latex paints.

The artificial latexes are latexes which are produced by the dispersion or redispersion of pre-formed water-insoluble polymers or solutions thereof. The artificial latexes are produced by known emulsification processes, e.g., by addition of water with stirring until phase inversion occurs, by high shear mixing with water at elevated temperatures or by dilution of a mixture of water and a water-miscible solvent followed by stripping to remove the solvent. A surfactant is required in the emulsification process unless hydrophilic groups are attached to the polymer in sufficient quantity to assist dispersion but in insufficient quantity to produce water-solubility.

Such artificial latexes are produced from polymers which are not prepared readily from monomers by emulsion polymerization, either because no substantial polymerization at a commercially acceptable rate is obtained under usual emulsion polymerization conditions, such as with isobutene, or because a particular form of the polymerized monomer is desired, for example, stereospecific polyisoprene, stereospecific polybutadiene and the like. Representative pre-formed polymers are polymers and copolymers of the mono-olefins having from 2 to 20 carbon atoms such as ethylene, propylene, 1-butene, 2-butene, isobutene, pentene, hexene, octene, dodecene, hexadecene, octadecene and especially those mono-olefins having up to 8 carbon atoms. Especially common types are the various ethylene/propylene copolymers.

Illustrative of still other polymers which can be converted to artificial latexes are alkyd resins, block and graft copolymers; e.g., styrene/butadiene graft and block copolymers; epoxy resins such as the reaction products of epichlorohydrin and bisphenol-A; and thermosettable vinyl ester resins; e.g., the reaction products of approximately equivalent amounts of a polyepoxide and an unsaturated monocarboxylic acid such as acrylic acid and methacrylic acid or unsaturated fatty acids such as oleic acid.

The thickeners of this invention are advantageous for use with the water-based compositions according to the foregoing description and with compositions containing those materials, especially coating compositions of various types. Mixtures of two or more thickeners may be used, if desired. Of course the latex polymers used in coating compositions are preferably film-forming at temperatures below about 25° C., either inherently or through the use of plasticizers. Such coating compositions include water-based consumer and industrial paints; sizing, adhesives and other coatings for paper, paperboard, textiles; and the like.

Usually these latex coating compositions contain added pigments, fillers and extenders such as titanium dioxide, barium sulfate, calcium carbonate, clays, mica, talc, silica and the like. The novel liquid emulsion polymers described herein are compatible with most latex paint systems and provide highly effective and efficient thickening. Suitable results are obtained using about 0.05–5.0 weight percent of the liquid emulsion polymer based on total weight of solids, and preferably about 0.1–2.0 weight percent.

The aqueous compositions thickened with the liquid emulsion polymers of this invention preferably are those in which any dispersing or solvating liquid present consists of greater than 50 percent by weight of water.

The following examples illustrate further the present invention. Unless otherwise indicated, all parts and percentages are by weight.

EXAMPLE 1

Preparation of Vinyl Surfactant Esters

The following are typical procedures for the preparation of the vinyl surfactant ester (VSE).

A. Nonylphenoxypoly(ethyleneoxy)$_9$ethyl Methacrylate A stainless steel reactor was charged with 474 parts (0.68 mole) of nonylphenoxypoly(ethyleneoxy)$_9$ethanol (Igepal ® CO-660 from GAF), 0.31 part of hydroquinone and 0.16 part of Ionol ® (2,6-di-t-butyl-p-cresol from Shell Chemical Co.). Then 8.6 parts of 90±2 percent H$_2$SO$_4$ was added with stirring followed by 526 parts (6.1 moles) of methacrylic acid stabilized with monomethyl ether of hydroquinone (MEHQ). With a slow stream of air bubbling through the reactant mixture, the reactor was heated at 105° C. for two hours, cooled and then liquid product (VSE-1A) recovered. By liquid chromatographic analysis the neat product contained 47.2 weight percent surfactant ester (90 percent conversion), 4.8 weight percent unreacted surfactant, 46.8 weight percent excess methacrylic acid and 1.2 weight percent water, sulfuric acid and stabilizers.

The vinyl surfactant ester can be used neat for the preparation of the desired emulsion copolymers or the ester can be recovered by conventional means. For use in neat form, a conversion to vinyl ester of at least 30–40 percent is desirable to avoid too high free surfactant level in the subsequent emulsion polymerization. With a 4–10 fold excess of carboxylic acid monomer, 70–90 percent conversion can normally be obtained at 100°–120° C. in 2–4 hours.

Other strong acid catalysts including p-toluenesulfonic acid and strong acid cation exchange resins such as Dowex ® 50 (H+ form) can be used, but 90 percent H$_2$SO$_4$ is effective and convenient. Indeed, this general H$_2$SO$_4$ catalyzed process has been used with a wide variety of C$_8$-C$_{16}$ alkylphenoxypoly(ethyleneoxy)ethanols.

B. Nonylphenoxypoly(ethyleneoxy)$_{39}$ethyl Methacrylate

A mixture of 222 parts of nonylphenoxypoly(ethyleneoxy)$_{39}$ethanol, 384 parts of methacrylic acid, 0.06 part of hydroquinone and 0.08 part of Ionol ® was blended in a stirred glass reactor and 5.5 parts of concentrated H$_2$SO$_4$ was added as esterification catalyst. The mixture was slowly heated to 110° C., held at 110° C. for an additional 145 minutes and then cooled to give 611 parts of a neat ester (VSE-1B) containing 38 weight percent of the surfactant ester and 62 weight percent of unreacted methacrylic acid.

C. Dodecylphenoxypoly(ethyleneoxy)$_{10}$ethyl Methacrylate

A mixture of 74.4 parts (0.1 mole) of dodecylphenoxypoly(ethyleneoxy)$_{10}$ethanol (T-Det DD-11 from Hayworth Chemical Co.), 129 parts (1.5 moles) of methacrylic acid and 0.06 part each of hydroquinone and Ionol ® was blended in a stirred glass reactor and 1.8 parts concentrated H$_2$SO$_4$ added as esterification catalyst. The mixture was slowly heated to 112° C., held at 112° C. for an additional 165 minutes and then cooled to give 205 parts of a neat ester (VSE-1C) containing 40.5 weight percent of the surfactant ester and 59.5 weight percent of unreacted methacrylic acid.

D. n-Octyloxypoly(ethyleneoxy)$_{19}$ethyl Methacrylate

In a similar manner the n-octyl polyethylene glycol ether obtained by condensation of n-octanol with 20 moles of ethylene oxide was esterified with excess methacrylic acid using sulfuric acid as a catalyst. A conversion of about 90 percent was obtained in two hours at 110°–120° C.

E. Hexadecylpoly(ethyleneoxy)$_{39}$ethyl Methacrylate

A mixture of 148 parts (0.058 mole) of hexadecylpoly(ethyleneoxy)$_{39}$ethanol, 255 parts (2.98 moles) of methacrylic acid, 0.06 part of hydroquinone and 0.06 part of Ionol ® and 3.6 parts concentrated H$_2$SO$_4$ was heated at 100°–112° C. for two hours yielding 403.5 parts of a solution containing 37.7 percent of vinyl surfactant ester (VSE-1E) and 62.3 percent of excess methacrylic acid.

F. Methoxypropoxypoly(butyleneoxy)$_4$(ethyleneoxy)$_{19}$-ethyl Methacrylate

The direct sulfuric acid catalyzed esterification process of Example 1A was used to prepare the above ester from the monomethyl ether of propylene glycol (Dowanol ® PM from The Dow Chemical Company) condensed with four moles of butylene oxide and then 20 moles of ethylene oxide using an alkaline catalyst. The neat vinyl surfactant ester (VSE-1F) can be used without further purification in the preparation of the liquid emulsion copolymer.

Other mono $C_8$–$C_{20}$ alkyl glycol ether surfactants can be similarly esterified to provide vinyl surfactant esters with controlled hydrophilic-lipophilic balance.

EXAMPLE 2

Liquid Emulsion Polymerization Process

The following are typical procedures for the preparation of the liquid emulsion polymers.

LEP-2A—48.0 MAA/42.0 EA/10.0 VSE-1A

The polymerization is carried out in a stainless steel, jacketed reactor equipped with stirrer and feed pumps using the concurrent addition technology of Miller et al. U.S. Pat. No. 3,563,946 in which separate monomer mix and aqueous feed solutions are added concurrently to an initial aqueous reactor charge stirred at 90 rpm and preheated to a desired temperature. When the addition of monomer and aqueous initiator is completed, normally in about 2–4 hours, the emulsion is stirred an additional 1.5 hours to finish the polymerization. Then the reactor is cooled and the liquid emulsion polymer filtered through 100 and 200 mesh screens.

A typical recipe and reaction conditions are:

| (1) Initial Reactor Charge* | |
|---|---|
| 374.0 parts | Condensate water |
| 0.0075 part | Versenex ® 80 chelant (40% solids) |
| 2.0 parts | Gafac ® RE-610 anionic surfactant |
| (2) Monomer Mix - Feed Rate - 4 hours | |
| 48.0 parts | Methacrylic acid (MAA) |
| 42.0 parts | Ethyl acrylate (EA) |
| 10.0 parts | Vinyl surfactant ester (VSE-1A) |
| 6.0 parts | Igepal ® CO-530 nonionic surfactant |
| (3) Aqueous Feed Mix - Feed Rate - 4 hours | |
| 69.8 parts | Condensate water |
| 0.0025 part | Versenex ® 80 chelant (40%) |
| 0.4 part | Sodium hydroxide |
| 2.0 parts | Dowfax ® 2A1 anionic surfactant (45% solids) |
| 1.0 part | Gafac ® RE-610 |
| 0.5 part | Sodium persulfate |

*Notes:
Quantities are in parts by weight based on 100 parts total monomer
Versenex ® 80 - sodium diethylenetriaminepentaacetic acid, 40% active solids from The Dow Chemical Company
Gafac ® RE-610 - a nonylphenoxypoly(ethyleneoxy)phosphate ester in free acid form from GAF
VSE-1A - neat vinyl surfactant ester of Example 1A (100% active basis)
Igepal ® CO-530 - nonylphenoxypoly(ethyleneoxy)ethanol from GAF
Dowfax ® 2A1 - sodium dodecyldiphenyl ether disulfonate from The Dow Chemical Company Conditions:
Addition temperature—70° C.,
Agitation—230 rpm
Cookdown—80° C., 1.5 hours.

The resulting liquid emulsion polymer contained 20.1 weight percent solids at pH 3.5 and had a 1 percent aqueous solution viscosity in ammonium salt form at pH 9 of 400 cps (Brookfield Model LVT, #2 spindle, 12 rpm, 25° C.).

LEP-2B—42.0 MAA+6.0 IA/42.0 EA/10.0 VSE-1A

Using the same polymerization recipe and conditions, a liquid emulsion polymer was prepared in which 6 parts of itaconic acid was substituted for 6 parts of methacrylic acid. The resulting liquid product contained 19.9 weight percent solids at pH 3.5 and had a 1 percent aqueous solution Brookfield viscosity of 1090 cps in ammonium salt form.

LEP-2C-1—48.3 MAA/41.7 EA/10.0 VSE-1A

In like manner a copolymer of 48.3 MAA/41.7 EA/10.0 VSE-1A was prepared which contained 20.0 weight percent solids and had a 1 percent aqueous solution Brookfield viscosity of 390 cps in ammonium salt form (cf Figure).

LEP-2C-2, LEP-2C-3, LEP-2C-4 and LEP-2C-5

These liquid emulsion polymers differ from LEP-2C-1 in the proportion of components. The compositions are shown in Table I.

LEP-2D-1—42.0 MAA/37.2 EA/20.8 VSE-1B

Several runs were made in 2 liter or 2 gallon reactors using the process of LEP-2E and the methacrylic ester of nonylphenoxypoly(ethyleneoxy)$_{39}$ethanol (VSE-1B) and the above monomer mix. Very clean emulsion polymers were obtained after filtration, containing about 20 weight percent solids and having an average particle size of about 1100–1300 Å.

LEP-2D-2, LEP-2D-3, LEP-2D-4 and LEP-2D-5

These liquid emulsion polymers differ from LEP-2D-1 in the proportion of components. The compositions are shown in Table I.

LEP-2E—47.8 MAA/42.0 EA/10.2 VSE-1C

A stirred glass reactor was charged with 271 parts of water, 2.0 parts of Conco Sulfate 219 (sodium salt of ethoxylated, sulfated lauryl alcohol from Continental Chemical Co.) and 0.1 part of Versenex ® 80 (40 percent). The reactor charge was purged with nitrogen while stirring and was heated to 69° C.

A monomer mixture of 24.7 parts of methacrylic acid, 31.6 parts of ethyl acrylate, 19.0 parts of the product solution of Example 1-C containing 40.5 percent of vinyl surfactant ester-1D and 59.5 percent of methacrylic acid and 2.0 parts Conco Sulfate 219 was prepared in a dropping funnel.

To the preheated aqueous reactor charge was added 0.13 part of potassium persulfate and about 7 parts of the monomer mixture. Then the remainder of the monomer mixture was added over about 3 hours while keeping a reaction temperature of 69°–70° C. After stirring an additional 2.25 hours at 70° C., the liquid emulsion polymer was cooled and filtered. The product (341 parts) contained 21.4 percent solids and had a Brookfield viscosity of 9200 as a 1 percent aqueous solution in ammonium salt form.

LEP-2F—42.2 MAA/37.2 EA/20.6 VSE-1D

Using the general procedure of LEP-2A, a monomer mix of 42.2 parts of methacrylic acid, 37.2 parts of ethyl acrylate and 20.6 parts of octyloxypoly(ethyleneoxy)$_{19}$ethyl methacrylate (VSE-1D) was copolymerized to give a stable emulsion copolymer containing 21.7 percent solids and having a 1 percent Brookfield LVT viscosity of 450 cps when neutralized with NH$_4$OH.

LEP-2G-1—46.8 MAA/41.4 EA/11.8 VSE-1E

In a similar manner a monomer mix of 18.5 parts of methacrylic acid, 28.0 parts of ethyl acrylate, 21.0 parts of the solution from Example 1-E which contained 37.7 percent of hexadecyloxypoly(ethyleneoxy)$_{39}$-ethyl methacrylate (VSE-1E) and 62.3 percent of methacrylic acid and 0.2 part of dodecyl mercaptan was copolymerized at 59°-62° C. using 0.09 part potassium persulfate initiator to give a stable emulsion copolymer containing 20.5 percent solids and having a 1 percent Brookfield LVT viscosity of 450 cps when neutralized with NH$_4$OH.

LEP-2G-2 49.6 MAA/44.1 EA/6.3 VSE-1E

This liquid emulsion polymer differs from LEP-2G-1 in the proportion of components.

LEP-2H—48.3 MAA/41.7 EA/10.0 VSE-1F

In another run a copolymer of 48.3 MAA/41.7 EA/10.0 VSE-1F was prepared from the methoxypropoxypoly(butyleneoxy)(ethyleneoxy)ethyl methacrylate of Example 1-F. It contained about 20 weight percent solids and had a 1 percent aqueous solution Brookfield viscosity of 288 cps in ammonium salt form.

It was found that increasing the polymerization temperature from 60°-80° C. had little effect on product efficiency in paint. But, the thickening efficiency of these products decreased as the nonionic vinyl comonomer was changed from ethyl acrylate to butyl acrylate to 2-ethylhexyl acrylate and to methyl methacrylate. Thickening efficiency increased with increasing alkyl chain length from C$_8$-C$_{16}$ alkyl in the alkylphenoxy surfactant ester.

EXAMPLE 3

Use as a Thickener for Latex Paint

The utility of the new liquid emulsion polymers as a thickener for latex paint is illustrated by data obtained with several latex paint formulations and tests.

| Formulation 3A - Interior Flat Latex Paint | | |
|---|---|---|
| Ingredients* | Lbs | Gallons |
| A. Water | 300 | 36.06 |
| Pigment dispersant (25% Tamol ® 731) | 12 | 1.31 |
| Defoamer (Drew L-475) | 2 | 0.26 |
| Preservative (Dowicil ® 75) | 1 | 0.08 |
| Surfactant (Triton ® X-100) | 5 | 0.56 |
| Aluminum silicate (ASP-400) | 100 | 4.66 |
| CaCO$_3$ (snowflake white) | 125 | 5.54 |
| Titanium dioxide (Ti-Pure ® R-931) | 250 | 7.79 |
| B. Ethylene glycol | 25 | 3.00 |
| Glycol ether (Texanol) | 10 | 1.26 |
| Everflex E ® latex (55%) | 250 | 27.78 |
| C. LEP Thickener and water** | 95.6 | 11.47 |
| | 1175.6 | 99.77 |

*Notes:
Tamol ® 731 - sodium salt of maleic anhydride/diisobutylene copolymer from Rohm & Haas
Drew L-475 - liquid defoamer from Drew Chemical Corp., Parsippany, NJ 07054
Dowicil ® 75 - 1-(3-chloroallyl)-3,5,7-triaza-1-azoniaadamantane chloride to which sodium bicarbonate has been added, from The Dow Chemical Co.
Triton ® X-100 - octylphenoxypolyethoxyethanol from Rohm & Haas
ASP-400 - Pigment grade aluminum silicate from Engelhard Minerals & Chem Corp., Iselin, NJ
Snowflake White - Pigment grade calcium carbonate from Thompson, Weinmann & Co., Cartersville, GA 30120
Ti-Pure ® R-931 - TiO$_2$ pigment from duPont
Texanol - 2,2,4-trimethylpentanediol-1,3 monoisobutyrate from Eastman Chemical Products, Inc., Kingsport, TN 37662
Everflex E ® latex - vinyl acetate-acrylic copolymer latex, sometimes called "vinyl-acrylic latex" or less commonly - "vinyl-acrylate latex" from W. R. Grace Co.
**LEP Thickener - normally about 1.0-6.0 lbs (100% solids basis)/100 gal plus water to balance To prepare a stock paint base, the A ingredients are ground together at high speed for 20 minutes using a Cowles grinder. Then at reduced speed premixed ethylene glycol and glycol ether are added followed by the Everflex E ® latex. The liquid emulsion polymer thickener (20 percent solids) and appropriate amount of water can be added immediately or later as desired for test purposes.

| Formulation 3B - Interior Semigloss Latex Paint | | |
|---|---|---|
| Ingredients* | Lbs | Gallons |
| A. Water | 93 | 11.18 |
| Pigment dispersant (25% Tamol ® 731) | 11 | 1.20 |
| Defoamer (Nopco ® NDW) | 2 | 0.27 |
| Propylene glycol | 32 | 3.84 |
| Preservative (Dowicil ® 75) | 1.3 | 0.10 |
| Titanium dioxide (Ti-Pure ® R-900) | 275 | 7.95 |
| B. Defoamer (Nopco ® NDW) | 4 | 0.53 |
| Surfactant (Triton ® GR7M) | 2 | 0.23 |
| Surfactant (Dowfax ® 2A1) | 2 | 0.21 |
| Rhoplex ® AC 490 (46.5%) | 590 | 66.67 |
| Propylene glycol | 32 | 3.84 |
| Phenoxyethanol coalescing agent | 10 | 1.09 |
| C. LEP Thickener and water** | 74.0 | 8.87 |
| | 1128.3 | 105.98 |

*Notes:
Tamol ® 731 - sodium salt of maleic anhydride/diisobutylene copolymer from Rohm & Haas
Nopco ® NDW - nonionic liquid defoamer from Diamond Shamrock Chemical Process Div.
Dowicil ® 75 - 1-(3-chloroallyl)-3,5,7-triaza-1-azoniaadamantane chloride to which sodium bicarbonate has been added, from The Dow Chemical Co.
Ti-Pure ® R-900 - TiO$_2$ pigment from duPont
Triton ® GR7M - dioctyl sodium sulfosuccinate from Rohm & Haas
Dowfax ® 2A1 - sodium dodecyldiphenyl ether disulfonate from The Dow Chemical Co.
Rhoplex ® AC 490 - acrylic emulsion latex from Rohm & Haas
**LEP Thickener - normally about 1.0-6.0 lbs (100% solids basis)/100 gal plus water to balance To prepare a stock paint base, the A ingredients are ground together at high speed for 20 minutes using a Cowles grinder. Then at reduced speed the B ingredients including premixed propylene glycol and phenoxyethanol are added. The emulsion polymer thickener (20 percent solids) and the balance of the water can be added immediately or later as desired for test purposes.

Procedures

A. Thickener Addition—The liquid emulsion polymers can be incorporated in latex paints in several ways:
1. Addition of the emulsion polymer to the final paint as liquid dispersion with subsequent neutralization with aqueous NH$_4$OH (28 percent) to a pH>7.
2. Presolubilization of the dispersion by diluting it with water and then adding sufficient alkali (NH$_4$OH or NaOH) with agitation. Once a clear solution has been obtained this can be post added to the final paint.
3. Addition of the thickener to the pigment grind after the pigment has been dispersed and then the addition of sufficient alkali (NH$_4$OH or NaOH) to solubilize the thickener. It is recommended that the pigment grind be as dilute as possible prior to solubilization of the thickener dispersion.

For experimental purposes, addition of the liquid emulsion polymer to a stock base paint followed by pH adjustment as necessary is particularly convenient (Method 1).

B. Evaluation—Properties of paint thickened with the liquid emulsion polymers are evaluated using standard procedures recommended by ASTM Committee D-1 Subcommittee D-42 and paint companies for determining such properties as paint viscosity, stability, flow and leveling, brushability, spatter, hiding power, color compatibility and gloss. For research purposes, the following tests for the paint viscosity, flow and leveling are particularly useful:

1. Stormer Viscosity—(ASTM Method D 562-55). The paint viscosity is measured with a Stormer Viscosimeter 24 hours after preparation. A viscosity of about 85-105 Kreb Unit (KU) is desired for most commercial latex paints. Accelerated stability tests often use Stormer viscosity measurements at 25° C. of samples held at 120° F. (49° C.) for 2-4 weeks.

2. Leneta Leveling Test—(The Leneta Co., Ho-Ho-Kus, NJ 07423). A paint sample is drawn down using a Leneta leveling test blade and the dried paint film compared visually with eleven Leneta levelness standards numbered 0-10 with 10 being perfect leveling.

3. Leneta Anti-Sag Test—(The Leneta Co., Ho-Ho-Kus, NJ 07423). A presheared sample of paint is drawn down with the Leneta anti-sag meter on Leneta drawdown chart form 7B positioned horizontally on a flat glass or metal plate. The chart is then immediately placed in a vertical position with the paint stripes horizontal and left edge (thinnest stripe) at the top, and allowed to dry. Each stripe, ranging in wet film thickness from 3 to 12 mils, is considered as having the same rating number as the notch by which it has been applied. The highest number (thickest) stripe that does not touch the one below itself is referred to as the index stripe, and its number is the Anti-Sag index of the paint. The practical interpretation of ratings is empirical and strongly subjective. Optimum sag resistance depends on the type of coating, but in general, an index of 8 through 12 is considered good to excellent.

4. Scrub Resistance—ASTM Method D-2486-66T. This test is normally run without the shim and provides an accelerated measure of wall paints to scrub erosion.

5. Color Acceptance—A test paint is prepared by mixing 0.5 g of color tint with 24.5 g of formulated paint and drawn down on a primed-unprimed chart (Leneta 1B) using a 7 mil gap clearance blade. A 2-3 cm diameter circular area overlapping the primed-unprimed chart surface is rubbed with a finger until decided resistance is felt. The film is dried and rated as: (1) acceptable-no visual difference in rubbed area; (2) pigment flocculation-rubbed area lighter in color or (3) colorant flocculation-rubbed area darker in color.

6. Gloss—ASTM Method D-523-67 is used to measure the Gardner 60° gloss of paint test panels. A gloss rating of 30-65 generally desirable for interior semigloss latex paints.

C. Table I

Table I presents typical test results for an interior flat latex paint and an interior semigloss latex paint prepared as described for Formulations 3A and 3B using the representative liquid emulsion polymers described in Example 2.

Test results such as shown in Table I demonstrate the utility of the water-based liquid emulsion polymers described herein as a pH responsive thickener for aqueous compositions. By appropriate adjustment of monomer ratios, polymerization conditions and final product formulations, the liquid emulsion polymers can be tailored to give optimum thickening for many applications including particularly those containing natural, synthetic and artificial latexes.

TABLE I

| LIQUID EMULSION POLYMER IN LATEX PAINT | | | | | | | | | | |
|---|---|---|---|---|---|---|---|---|---|---|
| | Comonomers, Wt % (1)* | | | Emulsion Polymer (2)* | | Paint | Evaluation (3)* | | | |
| | | | | | | | LEP | Visc | | |
| LEP | (A) R COOH | (B) Co— | (C) VSE | % Solids | 1% Visc | Base | Wt | KU | LL | LAS |
| 2A | 48.0 MAA | 42.0 EA | 10.0 1A | 20.1 | 400 | 3A | 4.5 | 101 | 7 | 12 |
| | | | | | | 3B | 2.75 | 85 | 5 | 12 |
| 2B | 42.0 MAA +6.0 IA | 42.0 EA | 10.0 1A | 19.9 | 1090 | 3A | 3.0 | 86 | 7 | <3 |
| | | | | | | 3B | 2.5 | 79 | 5 | 12 |
| 2C-1 | 48.3 MAA | 41.7 EA | 10.0 1A | 19.8 | 390 | 3A | 4.5 | 99 | 5 | 12 |
| | | | | | | 3B | 2.5 | 82 | 5 | 12 |
| 2C-2 | 48.3 MAA | 31.7 EA | 20.0 1A | 19.8 | 310 | 3A | 4.5 | 94 | 6 | 12 |
| | | | | | | 3B | 2.5 | 79 | 5 | 12 |
| 2C-3 | 38.3 MAA | 51.7 EA | 10.0 1A | 20.1 | 870 | 3A | 4.5 | 96 | 5 | 12 |
| | | | | | | 3B | 2.5 | 81 | 5 | 12 |
| 2C-4 | 38.3 MAA | 41.7 EA | 20.0 1A | 19.8 | 220 | 3A | 4.5 | 83 | 7 | 10 |
| | | | | | | 3B | 2.5 | 78 | 5 | 12 |
| 2C-5 | 31.2 MAA +13.8 AA | 45.0 EA | 10.0 1A | 21.9 | 7300 | 3A | 5.0 | 101 | 6 | 12 |
| | | | | | | 3B | 2.75 | 106 | 5 | 12 |
| 2D-1 | 42.0 MAA | 37.2 EA | 20.8 1B | 21.6 | 1100 | 3A | 5.0 | 70 | — | — |
| | | | | | | 3B | 3.5 | 119 | — | — |
| 2D-2 | 42.1 MAA | 18.6 EA +18.6 S | 20.8 1B | 21.8 | 800 | 3A | 5.0 | 94 | 8 | 9 |
| | | | | | | 3B | — | — | — | — |
| 2D-3 | 42.0 MAA | 37.2 S | 20.8 1B | 21.5 | 600 | 3A | 5.0 | <60 | — | — |
| | | | | | | 3B | 3.5 | 83 | — | — |
| 2D-4 | 42.2 MAA | 32.6 EA +18.6 VAc | 6.6 1B | 19.8 | 100 | 3A | — | — | — | — |
| | | | | | | 3B | 5.0 | 106 | 3 | 12 |
| 2D-5 | 18.7 MAA +15.0 HEA | 55.1 EA | 11.5 1B | 20.1 | 18400 (5%) | 3A | — | — | — | — |
| | | | | | | 3B | — | — | — | — |
| 2E | 47.8 MAA | 42.0 EA | 10.2 1C | 21.4 | 9200 | 3A | 3.5 | 110 | 5 | 12 |
| | | | | | | 3B | 2.0 | 106 | 3 | 12 |
| 2F | 42.2 MAA | 37.2 EA | 20.6 1D | 21.7 | 450 | 3A | 5.0 | 77 | — | — |
| | | | | | | 3B | 5.0 | 98 | 3 | 12 |
| 2G-1 | 46.8 MAA | 41.4 EA | 11.8 1E | 20.5 | 21000 | 3A | 5.0 | 130 | 4 | 12 |
| | | | | | | 3B | 2.5 | 128 | 4 | 12 |
| 2G-2 | 49.6 MAA | 44.1 EA | 6.3 1E | 19.0 | 325 | 3A | 5.0 | 98 | 9 | 10 |
| | | | | | | 3B | 3.0 | 112 | 5 | 12 |

TABLE I-continued

| | LIQUID EMULSION POLYMER IN LATEX PAINT | | | | | | | | | |
|---|---|---|---|---|---|---|---|---|---|---|
| | Comonomers, Wt % (1)* | | | Emulsion Polymer (2)* | | Paint | Evaluation (3)* | | | |
| LEP | (A) R COOH | (B) Co— | (C) VSE | % Solids | 1% Visc | Base | LEP Wt | Visc KU | LL | LAS |
| 2H | 48.3 MAA | 41.7 EA | 10.0 1F | 20.0 | 288 | 3A | 4.5 | 102 | 3 | 12 |
| | | | | | | 3B | 2.5 | 93 | 4 | 12 |

*Notes:
(1) Comonomers, wt % based on total monomers
(A) MAA - methacrylic acid
IA - itaconic acid
AA - acrylic acid
(B) EA - ethyl acrylate
S - styrene
HEA - 2-hydroxyethyl acrylate
VAc - vinyl acetate
(C) Vinyl surfactant ester from
1A nonylphenoxypoly(ethyleneoxy)₉ethanol
1B nonylphenoxypoly(ethyleneoxy)₃₉ethanol
1C dodecylphenoxypoly(ethyleneoxy)₁₀ethanol
1D octyloxypoly(ethyleneoxy)₁₉ethanol
1E hexadecyloxypoly(ethyleneoxy)₃₉ethanol
1F methoxypropoxypoly(butyleneoxy)₄(ethyleneoxy)₁₉ethanol
(2) Liquid emulsion polymer 1 percent Brookfield Model LVT viscosity, pH 9, #2 spindle at 12 rpm, 25° C.
(3) Evaluation in latex paint base
Formulation 3A - interior vinyl acrylic flat latex paint
Formulation 3B - interior acrylate semigloss latex paint
LEP, wt lbs LEP thickener (100% solids basis)/100 gallons
Viscosity 24 hr Stormer viscosity, KU
LL Leneta Leveling 0-10
LAS Leneta Anti-Sag 0-12

D. Table II

Table II presents typical test results comparing two liquid emulsion polymer thickeners with three commercial cellulose ether thickeners commonly used in latex paints. The effective thickening observed even with a lower viscosity LEP product suggests association of the LEP thickener with other components of the paint formulation as well as hydration by water.

Further rheological study of the liquid emulsion polymers suggests a controlled interaction or association of the LEP with the latex and pigment particles as a significant factor in the improved film build (one coat hiding) and reduced spray and spattering from roller application.

TABLE II

| | COMPARISON OF THICKENERS | | | | | |
|---|---|---|---|---|---|---|
| Test | Thickener | 1% Visc. | Paint Base | Thickener wt | Haake Visc. | Visc. KU |
| 3D-1 | LEP-2A | 400 | 3A | 4.5 | 3.65 | 101 |
| | | | 3B | 2.75 | 0.9 | 85 |
| 3D-2 | LEP-2E | 9200 | 3A | 3.5 | — | 110 |
| | | | 3B | 2.0 | — | 106 |
| 3D-3 | HEC | 1100–1450 | 3A | 5.0 | — | 96 |
| | | | 3B | 3.25 | — | 94 |
| 3D-4 | HEMC | 800–1050 | 3A | 5.25 | — | 88 |
| | | | 3B | 3.5 | — | 91 |
| 3D-5 | MC-J | 1000–1500 | 3A | 4.5 | 1.75 | 95 |
| | | | 3B | 2.5 | 1.3 | 80 |

Notes*:
LEP-2A: 48.0 MAA/42.0 EA/10.0 VSE-1A
LEP-2E: 47.8 MAA/42.0 EA/10.2 VSE-1C
HEC: Hydroxyethyl cellulose QP 15,000 (Union Carbide Corp)
HEMC: Hydroxyethyl methylcellulose XD-7603.03 (The Dow Chemical Co.)
MC-J: Hydroxypropyl methylcellulose Methocel® J20MS (The Dow Chemcial Co.)
Paint Base: Formulation 3A or 3B
Thickener, wt: Lbs (100% solids)/100 gal
Haake visc.: Viscosity (poise) at 10,000 sec$^{-1}$
Visc. KU: 24 hr Stormer viscosity E. To illustrate a more detailed evaluation of a liquid emulsion polymer as a thickener for a latex paint, Table III presents typical data for the liquid emulsion polymer described in Example 2A (48.0 MAA/42.0 EA/10.0 VSE-1A; 20.1 percent solids, 1 percent viscosity of 305 cps at pH 9.0) used as a thickener in two paint formulations. For comparison, similar data for a commercial cellulose ether thickener is also given. Note that the liquid emulsion polymer is more efficient as a thickener, provides improved flow and leveling with markedly reduced spattering and yet retains many of the desirable properties of the cellulose ether thickener.

TABLE III

| | LATEX PAINT PERFORMANCE | | | |
|---|---|---|---|---|
| Paint Type | Vinyl-Acrylic Flat | | Acrylic Semigloss* | |
| Thickener | LEP-2A | MC-J | LEP-2A | MC-J |
| Loading (lbs/100 gal) | 4.5 | 4.5 | 2.5 | 2.5 |
| Stormer Visc. (24 hr KU) | 101 | 95 | 84 | 80 |
| Leneta Leveling | 7/10 | 4/10 | 5/10 | 4/10 |
| Leneta Anti-Sag | 11/12 | 9/12 | 12/12 | 12/12 |
| Gardner 60° Gloss | — | — | 43 | 43 |
| Scrub (cycles) | 463[1] | 658[1] | 1075[2] | 1081[3] |
| Color Acceptance[4] | OK | OK | OK | Poor |
| Stormer Visc. (4 wks, 120° F.; KU) | 103–107 | 95 | 81 | 94–92 |
| Paint pH | 9.4 | 8.5 | 9.2 | 9.1 |
| Spattering | Minimal | Excessive | Minimal | Excessive |

Notes*:
Vinyl-Acrylic Interior Flat Latex - Formulation 3A
Acrylic Semigloss Latex - Formulation 3B
MC-J - Methocel® J20MS (The Dow Chemical Company)
[1]Avg. of 4 tests
[2]Avg. of 2 tests
[3]One test
[4]Color acceptance: Borden Aquablak G; Tenneco Thalo Blue, Thalo Green and Medium Yellow - Rubbed up.

EXAMPLE 5

LEP Thickeners in Other Aqueous Systems

The wide utility of the liquid emulsion polymers as thickeners for aqueous compositions including inorganic solutions and slurries is indicated by data such as the following:

A. Varying amounts of several inorganic salts were added to 1 percent aqueous solutions of LEP-2A (pH 9) and the Brookfield viscosity of the resulting solutions determined. Typical results are shown in Table IV.

TABLE IV

| Salt | VISCOSITY, CPS AT 25° C., pH 9 | | | | |
|---|---|---|---|---|---|
| | Conc: | | | | |
| | 0% | 0.25% | 0.50% | 0.75% | 1.00% |
| NaCl | 300 | 1090 | 1200 | 1125 | 850 |
| Na$_2$SO$_4$ | 300 | 780 | 910 | 920 | 905 |
| MgCl$_2$ | 300 | >2500 | 470 | Floc | — |

B. To a slurry of 48.8 g of titanium dioxide (Ti-Pure ® R-931 from duPont) and 50.2 g water having a 1 percent Brookfied viscosity of about 100 cps was added 51.0 g of a 2 percent aqueous solution of LEP-2A having a pH of about 9 and a 1 percent Brookfield viscosity of 300 cps. The resulting thickened slurry had a 1 percent Brookfield viscosity of 4200 cps.

C. The effect of LEP-2A as a thickener for several unformulated vinyl-acrylic paint latexes was determined using several commercial latexes blended with a 2 percent aqueous solution of LEP-2A neutralized to pH 9 with NH$_4$OH. The blended aqueous compositions were adjusted to 21 percent total solids and Brookfield viscosities were determined with results shown in Table V.

TABLE V

| Latex* | BROOKFIELD VISCOSITY* | |
|---|---|---|
| | Initial | 2% LEP-2A |
| Everflex ® E | 10 cps | 170 cps |
| Airflex ® 500 | 7.5 cps | 600 cps |
| Ucar ® 366 | 10 cps | 290 cps |

*Everflex ® E -Vinylacrylic copolymer (55% solids; W. R. Grace & Co.)
Airflex ® 500 - Vinyl acetate-ethylene latex (55% solids; Air Products & Chemicals)
Ucar ® 366 - Vinyl acetate-acrylic copolymer latex, sometimes called "vinyl-acrylic latex" (55% solids; Union Carbide Corp.)
Brookfield Viscosity #2 Spindle, 12 rpm, 25° C., pH 9.0

I claim:

1. A liquid emulsion polymer useful as a pH responsive thickener for aqueous compositions comprising an aqueous emulsion copolymer of:

A. about 15–60 weight percent based on total monomers of at least one C$_3$–C$_8$ α,β-ethylenically unsaturated carboxylic acid monomer of the formula:

$$\underset{\text{RCH}=\overset{\overset{\displaystyle R'}{|}}{C}-\text{COOH}}{} \quad (I)$$

where

R is H and R' is H, C$_1$–C$_4$ alkyl, or —CH$_2$COOX;
R is —COOX and R' is H or —CH$_2$COOX; or,
R is CH$_3$ and R' is H; and
X is H or C$_1$–C$_4$ alkyl;

B. about 15–80 weight percent of at least one nonionic, copolymerizable C$_2$–C$_{12}$ α,β-ethylenically unsaturated monomer of the formula:

$$\text{CH}_2=\text{CYZ} \quad (II)$$

where

Y is H and Z is —COOR, —C$_6$H$_4$R', CN, Cl,

or —CH=CH$_2$;
Y is CH$_3$ and Z is —COOR, —C$_6$H$_4$R', CN or —CH=CH$_2$; or

Y and Z are Cl; and
R is C$_1$–C$_8$ alkyl or C$_2$–C$_8$ hydroxyalkyl;
R' is H, Cl, Br, or C$_1$–C$_4$ alkyl; and
R" is C$_1$–C$_8$ alkyl; and C. about 1–30 weight percent based on total monomers of at least one nonionic vinyl surfactant ester of the formula:

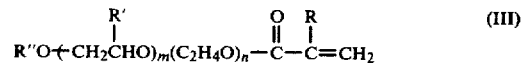

where

R is H or CH$_3$, each R' is C$_1$–C$_2$ alkyl,
R" is C$_8$–C$_{20}$ alkyl or C$_8$–C$_{16}$ alkylphenyl,
n is an average number from about 6–100 and m is an average number from about 0–50 provided that n≧m and Σ(n+m) is about 6–100;

said polymer being stable as an aqueous colloidal dispersion at a pH lower than about 5.0 but becoming an effective thickener for aqueous systems upon adjustment to a pH of about 5.5–10.5 or higher.

2. The polymer of claim 1 where the carboxylic acid monomer (A) is methacrylic acid, acrylic acid, or a mixture thereof with fumaric or itaconic acid.

3. The polymer of claim 1 containing about 33–55 weight percent of methacrylic acid or a mixture thereof with a minor amount of itaconic acid.

4. The polymer of claim 1 where the comonomer (B) is a monovinyl ester or a mixture thereof with styrene, 2-hydroxyethyl acrylate, acrylonitrile, vinyl chloride or vinyl acetate.

5. The polymer of claim 1 where the comonomer (B) is ethyl acrylate.

6. The polymer of claim 1 where the amount of the carboxylic acid monomer (A) is from about 25 weight percent to about 60 weight percent.

7. The polymer of claim 6 where the vinyl surfactant ester is selected from the group consisting of:

(1) alkylphenoxypoly(ethyleneoxy)ethyl acrylates of the formula:

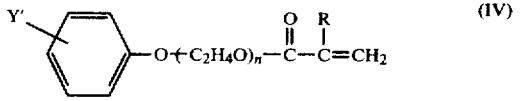

where

R is H or CH$_3$; Y' is C$_8$–C$_{16}$ alkyl, and n is about 6–100;

(2) alkoxypoly(ethyleneoxy)ethyl acrylates of the formula:

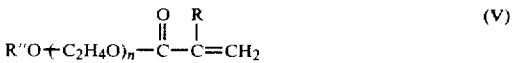

where

R is H or CH$_3$, R" is C$_8$–C$_{20}$ alkyl, and n is about 6–50; and (3) alkoxypoly(alkyleneoxy)ethyl acrylates of the formula:

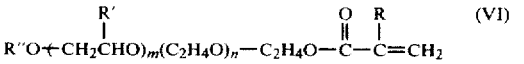

where

R is H or CH₃, each R' is C₁–C₂ alkyl,
R" is C₈–C₂₀ alkyl, and,
n is about 6–50 and m is about 1–40.

8. The polymer of claim 1 consisting essentially of:
A. about 35–55 weight percent of methacrylic acid, acrylic acid or mixtures thereof with fumaric or itaconic acid;
B. about 35–50 weight percent of ethyl acrylate or mixtures thereof with styrene, 2-hydroxyethyl acrylate, acrylonitrile, vinyl chloride or vinyl acetate; and
C. about 2–20 weight percent of a vinyl surfactant ester of Formula III.

9. The polymer of claim 8 wherein the vinyl surfactant ester is an alkylphenoxypoly(ethyleneoxy)ethyl acrylate of the formula:

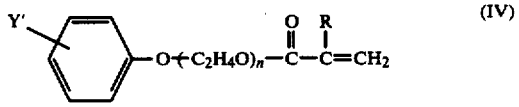

where
R is H or CH₃; Y' is C₈–C₁₆ alkyl, and n is about 6–100.

10. The polymer of claim 8 wherein the vinyl surfactant ester is an alkoxypoly(ethyleneoxy)ethyl acrylate of the formula:

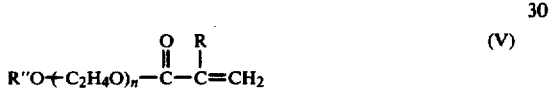

where R is H or CH₃, R" is C₈–C₂₀ alkyl, and n is about 6–50.

11. The polymer of claim 8 wherein the vinyl surfactant ester is an alkoxypoly(alkyleneoxy)ethyl acrylate of the formula:

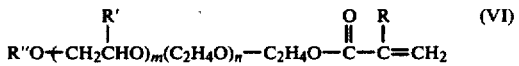

where
R is H or CH₃, each R' is C₁–C₂ alkyl,
R" is C₈–C₂₀ alkyl, and,
n is about 6–50 and m is about 1–40.

12. The polymer of claim 1 consisting essentially of:
A. about 40–50 weight percent of methacrylic acid;
B. about 35–50 weight percent of ethyl acrylate; and
C. about 2–12 weight percent of the methacrylic ester of a nonylphenoxypoly(ethyleneoxy)ₙethanol where n is about 6–40.

13. The polymer of claim 12 wherein about 1–15 weight percent of itaconic acid based on the total monomeric weight is substituted for a minor portion of the methacrylic acid.

14. The polymer of claim 13 containing about 40–45 weight percent of methacrylic acid and 2–10 weight percent of itaconic acid.

15. The polymer of claim 1 having an average particle size of about 500–3000 Å and a Brookfield viscosity of about 50–50,000 cps as a 1 percent aqueous solution in ammonium salt form at pH 9.0 and 25° C.

16. A liquid aqueous colloidal dispersion useful as a pH responsive polymeric thickener for aqueous compositions and containing about 10–50 weight percent of the polymer of claim 1 and having a pH of about 2.5–5.0.

17. The liquid aqueous colloidal dispersion of claim 16 where the polymer consists essentially of:
A. about 40–50 weight percent of methacrylic acid;
B. about 35–50 weight percent of ethyl acrylate; and
C. about 2–12 weight percent of the methacrylic ester of a nonylphenoxypoly(ethyleneoxy)ₙethanol where n is about 6–40.

18. A process for making the liquid aqueous colloidal dispersion of claim 16 comprising emulsion copolymerizing the monomeric mixture at a pH of about 2.5–5.0 in the presence of a free-radical producing initiator at a temperature between about 60°–90° C.

19. The process of claim 18 wherein the emulsion copolymerization gives a polymer having an average particle size of about 500–3000 Å and a Brookfield viscosity of about 50–50,000 cps as a 1 percent aqueous solution in ammonium salt form at pH 9.0 and 25° C.

20. The process of claim 18 wherein the monomeric mixture consists essentially of:
A. about 40–50 weight percent of methacrylic acid;
B. about 35–50 weight percent of ethyl acrylate or a mixture thereof with styrene, 2-hydroxyethyl acrylate, acrylonitrile, vinyl chloride, or vinyl acetate; and
C. about 2–12 weight percent of the methacrylic ester of an alkylphenoxypoly(ethyleneoxy)ethyl acrylate of the formula:

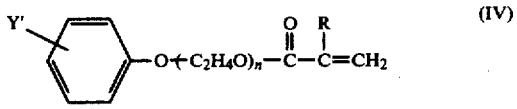

where R is H or CH₃; Y' is C₈–C₁₆ alkyl, and n is about 6–100.

21. A thickened aqueous composition having a pH within the range of about 6.5–11.0 comprising an aqueous composition containing a water-soluble or dispersible material and an effective amount of a liquid emulsion polymer of claim 1.

22. The thickened aqueous composition of claim 21 wherein the aqueous composition is a slurry of titanium dioxide.

23. The thickened aqueous composition of claim 21 wherein the aqueous composition is a colloidal dispersion of a water-insoluble polymer.

24. The thickened aqueous composition of claim 21 wherein the aqueous composition is a natural, synthetic or artificial latex.

25. The thickened aqueous composition of claim 21 wherein the liquid emulsion polymer consists essentially of:
A. about 40–50 weight percent of methacrylic acid;
B. about 35–50 weight percent of ethyl acrylate; and
C. about 2–12 weight percent of the methacrylic ester of a nonylphenoxypoly(ethyleneoxy)ₙethanol where n is about 6–40.

26. A process for making a thickened aqueous composition which comprises:
(1) blending with the aqueous composition a sufficient amount of the liquid emulsion polymer of claim 1 to thicken the aqueous coating composition and
(2) adjusting the pH of said blend within a range of about 6.5–11.0 as necessary to dissolve the emulsion polymer therein and thus thicken the aqueous composition.

27. The process of claim 26 wherein the aqueous composition is a colloidal dispersion of a water-insoluble polymer.

28. The process of claim 26 wherein the aqueous composition is a natural, synthetic or artificial latex.

29. The process of claim 26 wherein the aqueous composition is a synthetic latex.

30. The process of claim 26 wherein the liquid emulsion polymer consists essentially of:

A. about 40–50 weight percent of methacrylic acid;

B. about 35–50 weight percent of ethyl acrylate; and

C. about 2–12 weight percent of the methacrylic ester of an alkylphenoxypoly(ethyleneoxy)ethyl acrylate of the formula:

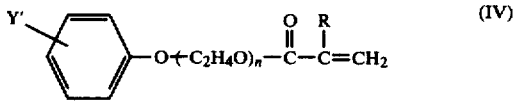

where R is H or $CH_3$; Y' is $C_8$–$C_{16}$ alkyl; and n is about 6–100.

* * * * *